United States Patent [19]
Dillard, III et al.

[11] Patent Number: 5,308,332
[45] Date of Patent: May 3, 1994

[54] ACTUATOR SPRING FOR SYRINGE SHEATHS

[75] Inventors: John A. B. Dillard, III, Camarillo; James A. Orr, Goleta, both of Calif.

[73] Assignee: Square One Medical, LP, Camarillo, Calif.

[21] Appl. No.: 7,261

[22] Filed: Jan. 21, 1993

Related U.S. Application Data

[62] Division of Ser. No. 901,095, Jun. 19, 1992, abandoned.

[51] Int. Cl.⁵ .............................................. A61M 5/00
[52] U.S. Cl. .................................. 604/110; 604/198; 604/263
[58] Field of Search ............... 604/198, 192, 187, 110, 604/263

[56] References Cited

U.S. PATENT DOCUMENTS

| 4,850,968 | 7/1989 | Romano | 604/198 X |
| 4,894,055 | 1/1990 | Sudnak | 604/110 X |
| 4,932,940 | 6/1990 | Walker et al. | 604/198 X |
| 4,985,021 | 1/1991 | Straw et al. | 604/198 |

Primary Examiner—John D. Yasko
Attorney, Agent, or Firm—Ladas & Parry

[57] ABSTRACT

This invention relates to reciprocable sheaths for hypodermic syringes that have latches to hold the sheaths over the needle of the syringes. A spring is employed to normally move the sheath over the needle and the expansion of the spring is limited to 90° of the free expansion dimension to positively move the sheaths and latches to the fully protected position. Volume numbers and graduations are placed on the exterior of the syringe plumger for greater clarity of reading.

3 Claims, 1 Drawing Sheet

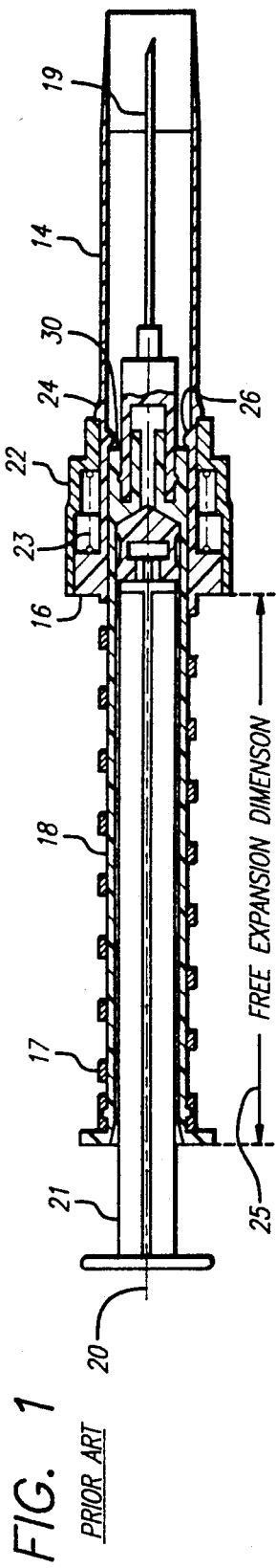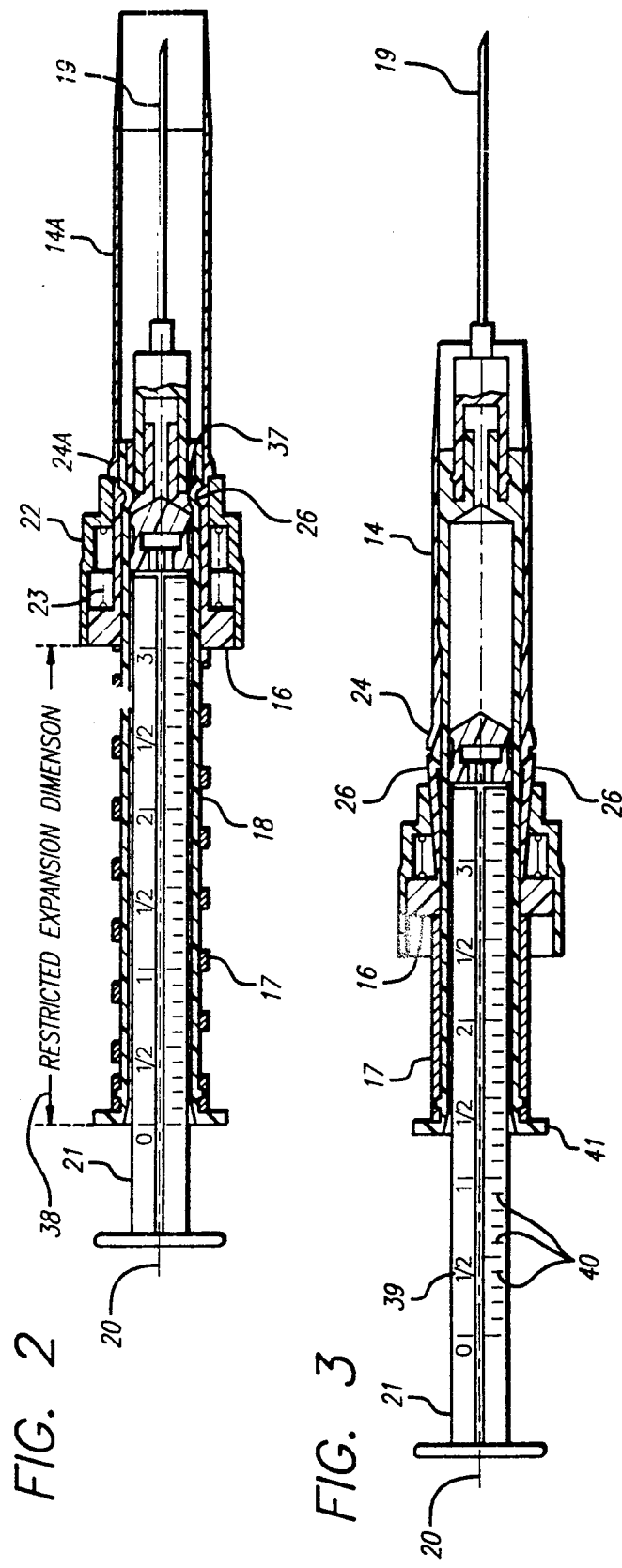
FIG. 1 PRIOR ART
FIG. 2
FIG. 3

ACTUATOR SPRING FOR SYRINGE SHEATHS

This is a divisional of co-pending application Ser. No. 07/901,095 filed Jun. 19, 1992 now abandoned.

This invention relates to sliding sheaths for hypodermic syringes and has particular reference to a ratio of spring expansion to free spring dimension for actuating the latch for the sliding sheaths.

BACKGROUND OF THE INVENTION

This invention relates to an improvement on the sliding sheath latch mechanism of the general type shown in U.S. Pat. No. 5,057,086 granted Oct. 15, 1991, to John A.B. Dillard and James A. Orr.

In that patent there is disclosed a sliding sheath that automatically covers the needle of a syringe when the operator finishes use. A latch mechanism maintains the sheath in its needle-covering position so that a person cannot accidentally prick himself or another person with the newly contaminated needle. The syringe sheath is propelled to its needle-covering position by a spring, preferably helical, carried on the exterior of the syringe body. During use of the syringe the operator manually pulls back the sheath to expose the needle by compressing the spring. When the operator has completed use of the syringe, he manually releases the sheath and the spring propels the sheath forwardly. The latch mechanism is activated by the same expansion of the spring to latch the sheath in its needle-covering position. Normally, the operator completely releases the sheath, and the spring slams the latch to the needle-covering position.

A problem sometimes arises, however, when the operator gently allows the spring to expand to extend the sheath over the needle. The last stages of spring expansion under this condition has such little force left that it sometimes does not actuate the latch, and the sheath can then slide under the impact of a blow, exposing the needle tip.

BRIEF DESCRIPTION OF THE INVENTION

The spring can be made stronger to get more terminal expansion force. However, this requires a larger, more costly spring. We have discovered that the same spring can be employed if its expansion stroke is limited. This retains sufficient terminal force to positively actuate the latch mechanism even when the expansion is gently guided by the fingers of the operator. The spring expansion generally can be limited to 90% of the free expansion dimension of the spring, which is presently preferred, although lesser expansions are satisfactory, such as 85%.

DESCRIPTION OF THE DRAWINGS

Referring to the drawings forming an integral part of this specification:

FIG. 1 shows a prior art syringe of the type of Pat. No. 5,057,086 and is a sectional view of a hypodermic syringe with a dimension marked for the free expansion of the spring that projects the inner latch fingers and the sheath.

FIG. 2 is a sectional view of a modified form of the syringe of FIG. 1 which restricts the spring expansion, and this restricted expansion dimension is marked.

FIG. 3 is a sectional view of the prior art syringe of FIG. 1 showing volume numbers and graduations marked on the piston of the syringe.

DETAILED DESCRIPTION OF THE DRAWINGS

Referring to the prior art of FIG. 1, a hypodermic syringe 10 has a reciprocable sheath 14, a latch base 16, and an expansion spring 17. These three parts may be formed of a single piece of material, such as an injection plastic molding. The sheath 14 reciprocates on a hollow syringe body 18 having a hollow needle 19 connected to one end and a manually operated plunger 21 on the other. When there is liquid in the syringe body 18, manually pressing the plunger to the right results in ejecting the liquid through the hollow needle 19.

The syringe has a longitudinal axis 20 through the body 18 and needle 19. The latch mechanism has a reciprocating outer shell 22, which is urged to the right by an expansion spring 23, one end of which bears against the annular latch base 16. The movement to the right of the outer shell 22 is halted by tabs 24 cut from the sheath 14 and bent radially outwardly.

The latching action is accomplished by a pair of latch fingers 26 that normally spring radially outwardly, but are forced radially inwardly by the right end of the outer latch shell 22 when it is moved to the right as shown in FIG. 1. These fingers 26 are integrally connected to the sheath 14. When they are forced inwardly as shown in FIG. 1, they contact the right end 30 of the hollow syringe body 18, and this prevents the sheath 14 from moving to the left. The latch spring 23 normally urges the outer latch shell 22 to the right, which holds the sheath in its extended position as shown in FIG. 1.

When the operator is finished with the syringe, the spring 17 will cause the sheath 14 to cover the needle 19 as shown in FIG. 1. The latch spring 23 will move the latch shell 22 to the right, forcing the fingers 26 inwardly to hold the sheath in its extended or covering position. No amount of blows on the sheath will cause it to reciprocate. Therefore, if the syringe contacts other persons, they are completely safe from the needle 19.

Referring still to FIG. 1, the spring 17 is shown in its fully extended condition. This dimension of free expansion is designated by the numeral 25. If, after use, the operator instantly releases the latch shell 22, the spring 17 will slam the latch flange 16 and outer latch shell 22 to the right and fully extend the sheath 14 over the needle 19 as shown. The latch fingers 26 will be located to the right of the right end 30 of the syringe body 18. The outer latch shell or collar 22 is forced to the right by its spring 23, moving the latch fingers 26 inwardly. This position of parts shown in FIG. 1 prevents the sheath from moving to the left, thereby protecting persons from the needle 19 if the syringe accidentally contacts them.

If after use the operator through inadvertence or otherwise lets the spring 17 slowly expand to the fully expanded dimension 25, there is the possibility that friction during the last 5% or 10% of the movement will prevent the fingers 26 from being disposed opposite the right end 20 of body 18. In this event the sheath 14 is not latched, and, if the syringe strikes a person, the needle 19 might prick him.

To avoid this non-latching, the spring 17 can be made stronger, but this solution adds weight and cost to the syringe. We have discovered that the necessary force to overcome this non-latching can be obtained by using all of the same components as shown in FIG. 1. This modification is the grooving of the right end of the syringe body 18 so that the latch fingers 26 will engage the body at a point to the left of its end 20. Furthermore, this solution does not impair in any way the operation of the syringe.

Referring now to FIG. 2, the parts identical with FIG. 1 bear the same numeral designations. Formed near the right end of the syringe body 18 is an annual groove 37 into which fit the latch fingers 26. The movement of the outer latch shell to the right is limited by raised tab 24A, formed from bending outwardly the material of the sheath 14A. The sheath 14A must be made longer than the sheath 14 of FIG. 1 to accommodate this change in latching position of the latch fingers 26. The groove 37 and the sheath 14A are the only structural changes compared to FIG. 1. Therefore, all the engineering of FIG. 1 is employed in the FIG. 2 structure.

The restricted expansion of spring 17 in FIG. 2 is shown by dimension 38 on FIG. 2 designated "Restricted Expansion Dimension." This dimension 38 can be upwards to 90%, but we presently prefer that dimension 38 be 90% of dimension 25.

FIG. 3

Illustrated in FIG. 3 is a further improvement on the prior art syringe of FIG. 1. This improvement is the placing of graduation marks and volume numbers on the plunger, or piston, of the syringe rather than on the transparent syringe body which is the usual practice. These volume numbers and graduations are shown also as applied to the syringe of FIG. 2.

Referring to FIG. 3 wherein the similar parts have the same numbers as in FIG. 1, the plunger, or piston, 21 has volume numbers 39 and graduations 40 applied to the exterior of the plunger 21, thus giving maximum visibility. These are usually metric cubic centimeters and decimals thereof. The operator can inject the needle 19 into a bottle of medicine or other liquid and manually move the plunger to the left in FIG. 3 until a desired number 39 or graduation 40 appears at the left end of the syringe body 18. This left end preferably terminates in a transverse flange 41. The reading is clearly visible and therefore accurate volumes are obtained. This is in contrast to numbers and graduations applied to the syringe body, at which the end of the plunger must be viewed through the transparent syringe body, which is often more translucent than transparent. Also, external springs such as spring 17 interfere with reading numbers and graduations.

We have described our inventions with respect to the presently preferred embodiments as required by the patent statutes. Various modifications and improvements will be apparent to those skilled in the art. All such variations, modifications, changes, and improvements that come within the true spirit and scope of the invention are included within the scope of the attached claims.

We claim:
1. A hypodermic syringe having:
   a) a hollow tubular syringe body,
   b) a hollow needle communicating with the hollow of the syringe body,
   c) a reciprocal tubular needle sheath disposed on the exterior of the syringe body,
   d) a spring engaging the syringe body and the sheath and expandable to move the sheath to cover the needle and having a free expansion dimension, and
   e) a latch engaging the syringe body and the sheath to normally latch the sheath over the needle, characterized by said latch latching the body and sheath when the spring has expanded to not more than 90% of its free expansion dimension.

2. A hypodermic syringe comprising:
   a) a hollow tubular syringe body;
   b) a hollow needle communicating with the hollow of the syringe body;
   c) a reciprocal tubular needle sheath disposed on the exterior of the syringe body;
   d) a spring engaging the syringe body and the sheath and expandable to move the sheath to cover the needle and having a free expansion dimension, and
   e) a latch finger carried by the sheath and movable by the spring to a latching position on the syringe body;

characterized by said spring moving the latch finger to its latching position when the spring has expanded to not more than 90% of its free expansion dimension.

3. A syringe for use with a needle, said syringe comprising:
   (a) a hollow syringe body, said body having a fitting to which the needle may be fixed;
   (b) a reciprocal needle sheath disposed on the exterior of the syringe body;
   (c) a spring engaging the syringe body and the sheath and being expandable to move the sheath into a needle-covering position;
   (d) a latch engaging the syringe body and the sheath to normally latch the sheath over the needle in an extended position after the syringe has been used; and
   (e) said spring having sufficient propulsive force towards an end of its stroke to overcome said latch and cause said latch to engage the syringe body and the sheath after the syringe has been used even if movement of said sheath toward its extended position is initially manually retrained by a person using said syringe.

* * * * *